(12) United States Patent
Zhu et al.

(10) Patent No.: US 7,714,131 B2
(45) Date of Patent: May 11, 2010

(54) PROCESS FOR THE STEREOSELECTIVE PREPARATION OF (−)-HALOFENATE AND DERIVATIVES THEREOF

(75) Inventors: Yan Zhu, Foster City, CA (US); Peng Cheng, Union City, CA (US); Xin Chen, San Ramon, CA (US); Jingyuan Ma, Sunnyvale, CA (US); Zuchun Zhao, Pleasanton, CA (US)

(73) Assignee: Metabolex, Inc., Hayward, CA (US)

( * ) Notice: Subject to any disclaimer, the term of this patent is extended or adjusted under 35 U.S.C. 154(b) by 615 days.

(21) Appl. No.: 11/525,200

(22) Filed: Sep. 20, 2006

(65) Prior Publication Data

US 2007/0072858 A1 Mar. 29, 2007

Related U.S. Application Data

(60) Provisional application No. 60/720,300, filed on Sep. 23, 2005.

(51) Int. Cl.
*C07D 295/16* (2006.01)
*C07D 207/06* (2006.01)
(52) U.S. Cl. ........................ 544/387; 544/176; 548/450; 548/524
(58) Field of Classification Search .................. 548/524, 548/540; 544/176, 387
See application file for complete search history.

(56) References Cited

U.S. PATENT DOCUMENTS

| 3,378,582 A | 4/1968 | Bolhofer |
| 3,444,299 A | 5/1969 | Wood et al. |
| 3,469,009 A | 9/1969 | Klingbail |
| 3,517,050 A | 6/1970 | Bolhofer |
| 3,517,051 A | 6/1970 | Bolhofer |
| 3,558,778 A | 1/1971 | Klingbail |
| 3,658,829 A | 4/1972 | Nakamura et al. |
| 3,674,836 A | 7/1972 | Creger |
| 3,860,628 A | 1/1975 | Shuman |
| 3,876,791 A | 4/1975 | Hubbard et al. |
| 3,923,855 A | 12/1975 | Shuman |
| 3,953,490 A | 4/1976 | Shuman |
| 4,001,268 A | 1/1977 | Kovar et al. |
| 4,067,996 A | 1/1978 | Najer et al. |
| 4,146,623 A | 3/1979 | Parker |
| 4,214,095 A | 7/1980 | Thiele et al. |
| 4,250,191 A | 2/1981 | Edwards |
| 4,338,330 A | 7/1982 | Gillet et al. |
| 4,508,882 A | 4/1985 | Yoshida et al. |
| 4,528,311 A | 7/1985 | Beard et al. |
| 4,532,135 A | 7/1985 | Edwards |
| 4,714,762 A | 12/1987 | Hoefle et al. |
| 4,786,731 A | 11/1988 | Russell |
| 4,863,802 A | 9/1989 | Moore et al. |
| 4,891,396 A | 1/1990 | Avar et al. |
| 4,910,211 A | 3/1990 | Imamura et al. |
| 4,933,367 A | 6/1990 | Wolff et al. |
| 5,132,429 A | 7/1992 | Narita et al. |
| 5,284,599 A | 2/1994 | Iwaki et al. |
| 5,476,946 A | 12/1995 | Linker et al. |
| 5,496,826 A | 3/1996 | Watson et al. |
| 5,500,332 A | 3/1996 | Vishwakarma et al. |
| 5,516,914 A | 5/1996 | Winter et al. |
| 5,554,759 A | 9/1996 | Vishwakarma |
| 5,700,819 A | 12/1997 | Aotsuka et al. |
| 5,716,987 A | 2/1998 | Wille |
| 5,766,834 A | 6/1998 | Chen et al. |
| 5,859,051 A | 1/1999 | Adams et al. |
| 5,874,431 A | 2/1999 | Stevens et al. |
| 5,883,124 A | 3/1999 | Samid |
| 5,942,626 A | 8/1999 | Winter et al. |
| 6,013,659 A | 1/2000 | Goldfarb et al. |
| 6,034,246 A | 3/2000 | Stevens et al. |
| 6,037,493 A | 3/2000 | Mathey et al. |
| 6,069,272 A | 5/2000 | Crout et al. |
| 6,093,830 A | 7/2000 | Yadav et al. |
| 6,184,235 B1 | 2/2001 | Connor et al. |
| 6,201,000 B1 | 3/2001 | Luther et al. |
| 6,201,147 B1 | 3/2001 | Bornscheuer et al. |
| 6,242,464 B1 | 6/2001 | Haris et al. |
| 6,248,768 B1 | 6/2001 | Yamada et al. |
| 6,262,118 B1 | 7/2001 | Luskey et al. |
| 6,506,747 B1 | 1/2003 | Betageri et al. |
| 6,613,802 B1 | 9/2003 | Luskey et al. |
| 6,624,194 B1 | 9/2003 | Luskey et al. |
| 6,646,004 B1 | 11/2003 | Luskey et al. |
| 6,670,395 B1 | 12/2003 | Wille |
| 7,199,259 B2 | 4/2007 | Daugs |
| 2003/0220399 A1 | 11/2003 | Luskey et al. |
| 2004/0039053 A1 | 2/2004 | Luskey et al. |
| 2004/0204472 A1 | 10/2004 | Briggs |
| 2005/0033084 A1 | 2/2005 | Daugs |
| 2005/0075396 A1 | 4/2005 | Luskey et al. |

FOREIGN PATENT DOCUMENTS

| CA | 967978 | 5/1975 |
| EP | 0 077 938 A2 | 5/1983 |
| EP | 0 105 494 A2 | 4/1984 |
| EP | 0 306 708 A1 | 3/1989 |
| EP | 1 162 196 A1 | 12/2001 |
| FR | 1476525 A | 4/1967 |
| GB | 1182008 | 2/1970 |
| GB | 1403309 | 8/1975 |
| JP | 53-071071 | 6/1978 |
| JP | 60-109578 A | 6/1986 |
| JP | 53-015325 A | 11/1993 |
| WO | WO 92/17435 A1 | 10/1992 |
| WO | WO 98/23252 A1 | 6/1998 |
| WO | WO 99/11627 A1 | 3/1999 |
| WO | WO 00/35886 A2 | 6/2000 |
| WO | WO 00/35886 A3 | 6/2000 |
| WO | WO 00/74666 A2 | 12/2000 |
| WO | WO 00/74666 A3 | 12/2000 |
| WO | WO 02/44113 A2 | 6/2002 |
| WO | WO 02/44113 A3 | 6/2002 |
| WO | WO 2004/112774 A1 | 12/2007 |

OTHER PUBLICATIONS

Devine et al. Tetrahedron Letters 1996, 37(16), 2683-2686.*
Harpp et al. J. Org. Chem. 1975, 40, 3420.*
Aronow, W.S. et al., "Effect of Halofenate on Serum Uric Acid," Clin. Pharmacol. Ther., 1973, vol. 14, No. 3, pp. 371-373.
Aronow, W.S. et al., "Halofenate: An Effective Hypolipemia- and Hypouricemia-Inducing Drug," Current Therapeutic Research, 1973, vol. 15, No. 12, pp. 902-906.

Bardin, C.W. ed., *Current Therapy in Endocrinology and Metabolism* 6th Edition, Mosby—Year Book, Inc., St. Louis: MO, 1997, pp. 509-519

Barrett-Conner, O.E., "Epidemology, Obesity, and Mellitus", Epidemol. Rev.,1989, vol. 11, pp. 172-181.

Bassett, D.R. et al., "Effects of Halofenate and Probenecid in Serum Lipids and Uric Acid in Hyperlipidemic, Hyperuricemic Adults," Clin. Pharmacol. Ther. 1977, vol. 22, No. 3, pp. 340-351.

Bell, G.I. et al., "Glucokinase Mutations, Insulin Secretion, and Diabetes Mellitus," Annu. Rev. Physiol., 1996, vol. 58, No. pp. 171-187.

Berkow, R. et al. eds., "Disorders of Carbohydrate Metabolism," Chapter 94 *In The Merck Manual of Diagnosis and Therapy* 15th ed., Merck Sharp & Dohme Research Laboratories, 1987, pp. 1069-1072.

Bluestone, R. et al., "Halofenate its Selection and Trial as a Primary Uricosuric Agent," Arthritis Rheum., 1975, vol. 18, pp. 859-862.

Brooks, D.A. et al., "Design and Synthesis of 2-Methyl-2-4{4-{2-(5-methyl-2-aryloxazol-4-yl)ethoxy}phenoxy-propionic Acids: A New Class of Dual PPARα/y Agonists," J. Med. Chem., Dec. 15, 2001, vol. 44, pp. 2061-2064.

Chiasson, J-L. et al., "The Efficacy of Acarbose in the Treatment of Patients With Non-Insulin-Dependant Diabetes Mellitus," Annals of Intern. Med., 1994 vol. 121, No. 12, pp. 928-935.

Coniff, R. et al., "Acarbose: a Review of US Clinical Experience," Clinical Therapeutics, 1997, vol. 19, No. 1, pp. 16-26.

Coniff, R.F et al., "Multicenter, Placebo-Controlled Trial Comparing Acarbose (BAY g 5421) With Placebo, Tolbutamide, and Tolbutamide-Plus-Acarbose in Non-Insulin-Dependent Diabetes Mellitus," The American Journal of Medicine, May 1995, vol. 98, pp. 443-451.

Devine, P.N., "Stereoselective Synthesis of 2-Aryloxy Esters: an Asymmetric Approach to Fluoxetine, Tomoxetine and Nisoxetine," Tetrahedron, 1997, vol. 53, No. 20, pp. 6739-6746.

Diamant, M. et al., "Thiazolidinediones in Type 2 Diabetes Mellitus: Current Clinical Evidence," Drugs, 2003, vol. 63, No. 13, pp. 1373-1405, Abstract.

Dörfler, H. et al., "Primärer Verteilungsraum and Plasmahalbwertszeit von Intravenös Verbreichtem Insulin," Med. Poliklinik Univ. Muchen, 1973, pp. 1297-1299.

Edelman, S.V. et al., "Non-Insulin-Dependent Diabetes Mellitus", *In Current Therapy in Endocrinology and Metabolism* Sixth Edition, 1997, pp. 430-438.

El-Sherief, H.A. et al., "Synthesis and Antimicrobial Activities of Some New Benzimidazoles, Part I," Bull. Fac. Sci. Assiut Univ. B, 1995, vol. 24, No. 1, pp. 111-123.

Fajans, S.S. et al., "Maturity Obset Diabetes of the Young (MODY)" Diabetes Medicine, 1996, vol. 13, pp. S90-S95.

Fanelli, G.M., Jr. et al., "Renal Excretion and Uricosuric Properties of Halofenate A Hypolipidemic Uricosuric Agent in the Chimpanzee," J. Pharmacol. Exp. Ther., 1972, vol. 180, pp. 377-396.

Feldman, E.B. et al., "Effects of Halofenate on Glucose Tolerance in Patients with Hyperlipoproteinemia," Journal Clinical Pharmacology, May-Jun. 1978, vol. 18, pp. 241-248.

Feldman, E.B. et al., "Insulin Sensitivity in Hypertriglyceridemia: Induction by Combined Triglyceride and Uric Acid Lowering," Clinical Research, Jan. 1975, vol. 23, No. 1, p. 43A.

Flier, J.S., "Insulin Receptors and Insulin Resistance," Ann Rev. Med., 1983, vol. 34, pp. 145-160.

Friedberg, S.J., "The Control of Insulin Resistant and Refractory Type II Diabetes Mellitus by Means of Halofenate-Sulfonylurea Combined Regimen," Clinical Research, 1986, vol. 34, p. 682A.

Gavin III, J.R. et al., "Report of the Expert Committee on the Diagnosis and Classification of Diabetes Mellitus," Diabetes Care, Jan. 1999, vol. 22, Supplement 1, pp. S5-S19.

Goetze, S., et al., "PPARγ-Ligands Inhibit Migration Mediated by Multiple Chemoattractants in Vascular Smooth Muscle Cells," Journal of Cardiovascular Pharmacology, 1999, vol. 33, pp. 798-806.

Howard, B.V., et al., "Lipoprotein Composition in Diabetes Mellitus," Atherosclerosis, 1978, vol. 30, pp. 153-162.

Huang, X. et al., "Search for New Antiphytovirucides," J. Wuhan Univ. (Nature Science Edition), Apr. 1995, vol. 41, No. 2, pp. 142-148.

Hucker, H.B. et al., "Metabolism of a New Hypolipidemic Agent, 2-Acetamidoethyl (*p*-Chlorophenyl) (*m*-Trifluoromethylphenoxy)-Acetate (Halofenate) in the Rat, Dog, Rhesus Monkey and Man," The Journal of Pharmacology and Experimental Therapeutics, 1971, vol. 179, No. 2, pp. 359-371.

Hutchison, J.C. et al., "The Uricosuric Action of Halofenate (MK-185) in Patients with Hyperuricemia or Uncomplicated Primary Gout and Hyperlipidemia," Atherosclerosis, 1973, vol. 18, pp. 353-362.

International Search Report mailed Feb. 16, 2007, for PCT Application No. PCT/US06/36928 filed on Sep. 21, 2006, two pages.

Iwamoto, Y. et al., "Effect of Combination Therapy of Troglitazone and Sulphonylureas in Patients with Type 2 Diabetes Who Were Poorly Contorlled by Sulphonylurea Therapy Alone," Diabetic Medicine, 1996, vol. 13, pp. 365-370.

Jacques, J. et al., "Formation and Separation of Diasteromers." *In Enantiomers, Racemates, and Resolutions*, John Wiley & Sons, New York, 1981, pp. 251-328.

Jain, A. et al., "Potentiation of Hypoglycemic Effect of Sulfonylureas by Halofenate," New England J. of Med., Dec. 15, 1975, vol. 293, No. 25, pp. 1283-1286.

Jain, A. et al., "The Effect of MK-185 on Some Aspects of Uric Acid Metabolism," Clin. Pharmacol. Ther., Jul.-Aug. 1970, vol. 11, pp. 551-557.

Joslin, E.P., "Arteriosclerosis and Diabetes," Annals of Clinical Medicine, 1927, vol. 5, No. 12, pp. 1061-1079.

Keller, V.C. et al., "Die Benhandlung von Hyperlipidämie und Hyperurikärnie mit 2-Acetamidoäthyl-(4-chlorophenyI)-(3-trifluoromethylphenoxy)-acetat (Halofenat), einem Derivat des Clofibrat," *Arzneimittelforschung*, 1976, vol. 26, No. 12, pp. 2221-2224.

Knowler, W.C. et al., "Obesity in the Pima Indians: its magnitude and relationship with diabetes," Am. J. Clin. Nutr., 1991, vol. 53, pp. 1543S-1551S.

Kobayashi, M., et al., "Improvement of Glucose Tolerance in NIDDM by Clofibrate Randomized Double-Blind Study," Diabetes Care, Jun. 1988, vol. 11, No. 6, pp. 495-499.

Kohl, E.A. et al., "Improved Control of Non-Insulin-Dependent Diabetes Mellitus by Combined Halofenate and Chlorpropamide Therapy," Diabetes Care, Jan.-Feb. 1984 vol. 7, No. 1, pp. 19-24.

Kreisberg, R.A., "Hyperlipidemia," Current Therapy in Endocrinology and Metabolism 6th Edition, 1997, pp. 509-519.

Krut, L.H. et al., "Comparison of Clofibrate with Halofenate in Diabetics with Hyperlipidaemia," S.A. Med. J., 1977, pp. 348-352.

Kudzma, D.J. et al., "Potentiation of Hypoglycemic Effect of Chlorpropamide and Phenformin by Halofenate," Diabetes, Apr. 1977, vol. 26, No. 4, pp. 291-295.

Kuntznen V.O. et al., "Wirkung von Halofenat auf Triglycerid-und Harnsäurespiegel sowie auf Gerinnungsund Thrombozytenverhalten bei Patienten mit Hyperlipoproteinämie Typ IV und Hyperurikämie," Arzneimittelforschung, 1978, vol. 28, No. 12, pp. 2349-2352.

Kwiterovich, P. Jr., "State-of-the-Art Update and Review: Clinical Trials of Lipid-Lowering Agents," The American Journal of Cardiology, Dec. 1998, vol. 82, No. 12A, pp. 3U-17U.

Leroith, D. et al. eds., *Diabetes Mellitus*, Lippincott-Raven Publishers, Philadelphia: PA, 1996. (Table of Contents Only).

Lin, J.H. et al., "Inhibition and Induction of Cytochrome P450 and the Clinical Implications," Clin Pharmacokinet, Nov. 1998, vol. 35, No. 5, pp. 361-390.

Lisch, H.-J. et al., "Comparison of the Effects of Halofenate (MK-185) and Clofibrate on Plasma Lipid and Uric Acid Concentration in Hyperlipoproteinemic Patients," Atheroschlerosis, 1995, vol. 21, pp. 391-399.

Lochmüller, C.H. et al., "Chromatographic Resolution of Enantiomers." J. Chromatography, 1975, vol. 113, pp. 283-302.

Mahley, R.W. et al., "Disorders of Lipid Metabolism," Chapter 23 *In Williams Textbook of Endocrinology* 9th Edition, 1998, W.B. Sanders Company, Philadelphia: PA, pp. 1099-1153.

Malher, R.J., Clinical Review 102, "Type 2 Diabetes Mellitus: Update on Diagnosis, Pathophysiology, and Treatment," J. Clin. Endocrinol. Metab., 1999, vol. 84, No. 4, pp. 1165-1171.

Mandel, L.R., "Studies on the Mechanism of Action of Halofenate," Lipids, 1976, vol. 12, No. 1, pp. 34-43.

McMahon, F.G. et al., "Some Effects of MK-185 on Lipid and Uric Acid Metabolism in Man," Univ. Mich. Med. Center J., Oct.-Dec. 1970, vol. 36, No. 4, pp. 247-248.

Metabolex, The Diabetes Biopharmaceutical Company, "Metabolic Disease Drug Discovery & Development Summit," Strategic Research Institute, (May 6-7, 2002).

Miners, J.O. et al., "Cytochrome P4502C9: An Enzyme of Major Importance in Human Drug Metabolism," J Clin Pharmacol, 1998, vol. 45, pp. 525-538.

Morgan, J.P. et al., "Hypolipidemic, Uricosuric, and Thyroxine-displacing Effects of MK-185 (halofenate)," Clin. Pharmacol. Therap., 1971, vol. 12, No. 3, pp. 517-524.
Neuman, J., et al., "A Double-Blind Comparison of the Hypolipidemic and Hypouricemic Action of Halofenate and Clofibrate in Patients with Hyperlipoprteinemia," The International Cardiovascular Society, pp. 532-537, 1973.
Pelkonen, O. et al., "Inhibition and Induction of Human Cytochrome P450 (CYP) Enzymes," Xenobiotica, 1998, vol. 28, No. 12, pp. 1203-1253.
Qu, F. et al., "Search for New Antiphytovirucides," Wuhan Univ. Journal of National Science, 1998, vol. 3, No. 2, pp. 201-204.
Qu, F. et al., "Some New Antiphytoviral Compounds Containing Trifluoromethyl Group," Wuhan Univ. Journal of National Science, 1996, vol. 1, No. 2, pp. 283-284.
Ravenscoft, P.J. et al., "Studies of the Uricosuric Action of the Hypolipidemic Drug Halofenate," Clin. Pharmacol. Ther., Jul.-Aug. 1973, vol. 14, No. 4, pp. 547-551.
Read, J. et al., "The Complete Optical Resolution of Externally Compensated Acids and Bases," Journal of the Society of the Chemical Industry—London, Jan. 13, 1928, vol. 47, pp. 8T-11T.
Reaven, G.M., "Insulin Resistance and Human Disease: A Short History," J. Basic & Clin. Phys. & Pharm., 1998, vol. 9, No. 2-4, pp. 387-406.
Reaven, G.M., "Pathophysiology of Insulin Resistance in Human Disease," Physiol. Rev. Jul. 1995, vol. 75, No. 3, pp. 473-486.
Ryan, J.R., "The Metabolic Spectrum of Halofenate," Int. J. Clin. Pharmacol., 1975, vol. 12, No. 1/2, pp. 239-243.
Safak, C. et al., "Synthesis of Some Benzimidazol Derivatives, and Their Effects on Serum Total Cholesterol and Triglyceride Levels in Rats," FABAD J. Farm. Sci., 1983, vol. 8, pp. 19-29.
Schaeffer, S. "Trying to Beat PPAR," BioCentury, The Bernstein Report on BioBusiness, (Reprint from Jun. 14, 2004), pp. 1-3.
Schapel, G.J. et al., "Efficacy and Interactions of Oxandrolone, Halofenate and Clofibrate in a Factorial Study on Experimental Acute Nephrotic Hyperlipidemia," The Journal of Pharmacology and Experimental Therapeutics, 1975, vol. 194, No. 1, pp. 274-284.
Schlosstein, L.H. et al. "Studies with Some Novel Uricosuric Agents and Their Metabolites: Correlation Between Clinical Activity and Drug-Induced Displacement of Urate From its Albumin-Binding Sites," J. Lab. Clin. Med., Sep. 1973, vol. 82, No. 3, pp. 412-418.
Shi, G.Q., "Design and Synthesis of α-Aryloxyphenylacetic Acid Derivatives: A Novel Class of PPARαlγ Dual Agonists with Potent Antihyperglycemic and Lipid Modulating Activity," J. Med. Chem., 2005, vol. 48, pp. 4457-4468.
Sirtori, C. et al., "Clinical Evaluation of MK-185: A New Hypolipidemic Drug," Lipids, 1971, vol. 7, No. 2, pp. 96-99.
Skyler, J.S., "Glucose Control in Type 2 Diabetes Mellitus," Annals of Internal Medicine, Nov. 1, 1997, vol. 127, No. 9, pp. 837-838.
Steiner, A., et al., "A Comparative Review of the Adverse Effects of Treatments for Hyperlipidaemia," Drug Safety, 1991, vol. 6, No. 2, pp. 118-130.
Taskinen, M.-R., "Lipid Disorders in NIDDM: Implications for Treatment," Journal of Internal Medicine, 1998, vol. 244, pp. 361-370.
Trust, R. I. et al., "(Aryloxy)[p-(aryloxy)phenyl]- and (Aryloxy)[p-arylthio)phenyl]acetic Acids and Esters as Hypolipidemic Agents," Journal of Medicinal Chemistry, 1979, vol. 22, No. 9, pp. 1068-1074.
Turner, N. et al., "Insulin Resistance, Impaired Glucose Tolerance and Non-Insulin-Dependent Diabetes, Pathologic Mechanisms and Treatment: Current Status and Therapeutic Possibilities," Prog Drug Res., 1998, pp. 33-94.
Varma, R.S. et al., "Synthesis of Substituted 2-Phenylbenzothiazoles & 5(6)-Nitro-1, 3-disubsituted-benzimidazoline-2-thiones as CNS Active Agents," Indian Journal of Chemistry, May 1998, vol. 27B, No. 5, pp. 438-442.
Vedell, E.S., et al., "Differential Effects of Chronic Halofenate Administration on Drug Metabolism in Man," Fed. Proc., Mar.-Apr. 1972, vol. 31, No. 2, p. 538.
Wilson, J.D., et al. eds. Disorders of Lipid Metabolism, Chapter 23, Textbook of Endocrinology, 9th Edition, 1998, W.B. Sanders Company, Philadelphia: PA. (All References Cited Therein).
Wright, A.D., et al., "UKPDS 28: A Randomized Trial of Efficacy of Early Addition of Mefformin in Sulfonylurea-Treated Type 2 Diabetes," Diabetes Care, Jan. 1998, vol. 21, No. 1, pp. 87-92.

* cited by examiner

*Primary Examiner*—Rebecca L Anderson
*Assistant Examiner*—Jason M Nolan
(74) *Attorney, Agent, or Firm*—Townsend and Townsend and Crew LLP

(57) ABSTRACT

The present invention provides a compounds the formula (IV):

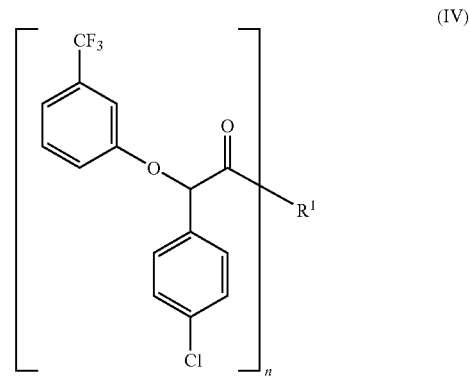

and methods for producing an α-(phenoxy)phenylacetic acid compound of the formula:

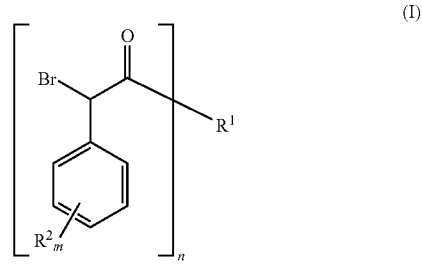

wherein $R^1$ is a member selected from the group consisting of:

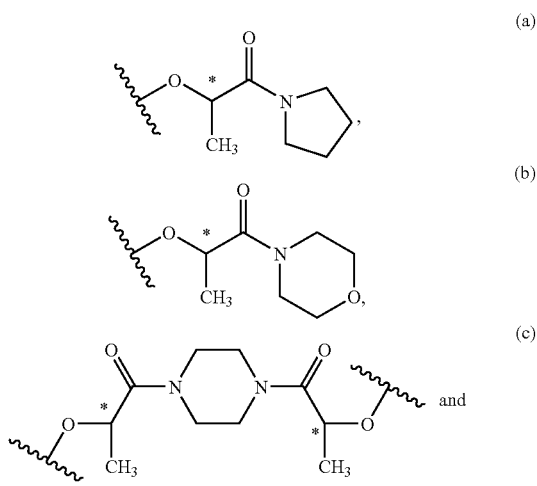

-continued

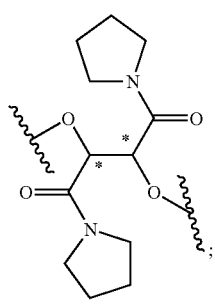

(d)

each $R^2$ is a member independently selected from the group consisting of $(C_1-C_4)$alkyl, halo, $(C_1-C_4)$haloalkyl, amino, $(C_1-C_4)$aminoalkyl, amido, $(C_1-C_4)$amidoalkyl, $(C_1-C_4)$sulfonylalkyl, $(C_1-C_4)$sulfamylalkyl, $(C_1-C_4)$alkoxy, $(C_1-C_4)$heteroalkyl, carboxy and nitro; the subscript n is 1 when $R^1$ has the formula (a) or (b) and 2 when $R^1$ has the formula (c) or (d); the subscript m is an integer of from 0 to 3; * indicates a carbon which is enriched in one stereoisomeric configuration; and the wavy line indicates the point of attachment of $R^1$; and compounds.

16 Claims, No Drawings

PROCESS FOR THE STEREOSELECTIVE PREPARATION OF (−)-HALOFENATE AND DERIVATIVES THEREOF

CROSS-REFERENCES TO RELATED APPLICATIONS

This application claims the benefit of U.S. Patent Application No. 60/720,300, filed Sep. 23, 2005, the content of which is incorporated herein by reference.

FIELD OF THE INVENTION

The present invention relates to a stereoselective process for the preparation of (−)-halofenate (4-Chloro-α-(3-trifluoromethylphenoxy)phenylacetic acid) and intermediates thereof.

BACKGROUND OF THE INVENTION

Esters and amides derivatives of (−)-4-Chloro-α-(3-trifluoromethylphenoxy)phenylacetic acid (halofenic acid) are chiral compounds and are useful in ameliorating a variety of physiological conditions, including conditions associated with blood lipid deposition, Type II diabetes and hyperlipidema (see, e.g., U.S. patent application Ser. No. 10/656,567 and U.S. Pat. No. 6,262,118 which are incorporated herein by reference in their entirety). Halofenic acid contains a single chiral center at an asymmetrically substituted carbon atom alpha to the carbonyl carbon atom, and therefore exist in two enantiomeric forms. It has been found that the (−)-enantiomer of halofenic acid is about twenty-fold less active in its ability to inhibit cytochrome P450 2C9 compared to the (+)-enantiomer. Id. Administration of a racemic halofenic acid or its derivatives can lead to a variety of drug interaction problems with other drugs, including anticoagulants, anti-inflammatory agents and other drugs, that are metabolized by this enzyme. Id. It is desirable to administer the (−)-enantiomer of halofenic acid or its derivatives which is substantially free of the (+)-enantiomer to reduce the possibility of drug interactions. Thus, enantiomerically enriched forms of α-(phenoxy) phenylacetic acids or its derivatives are valuable chemical intermediates for the preparation of pharmaceutical compounds.

As shown below, various synthetic routes for making α-(phenoxy)phenylacetic acid derivatives have been reported in literature. Unfortunately, these molecules are often difficult to be produced with high enantiomeric purity and in high yields by known synthetic methods.

Scheme 1. Synthesis of α-(phenoxy)phenylacetic acids.

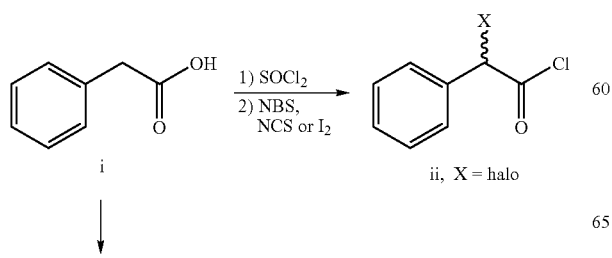

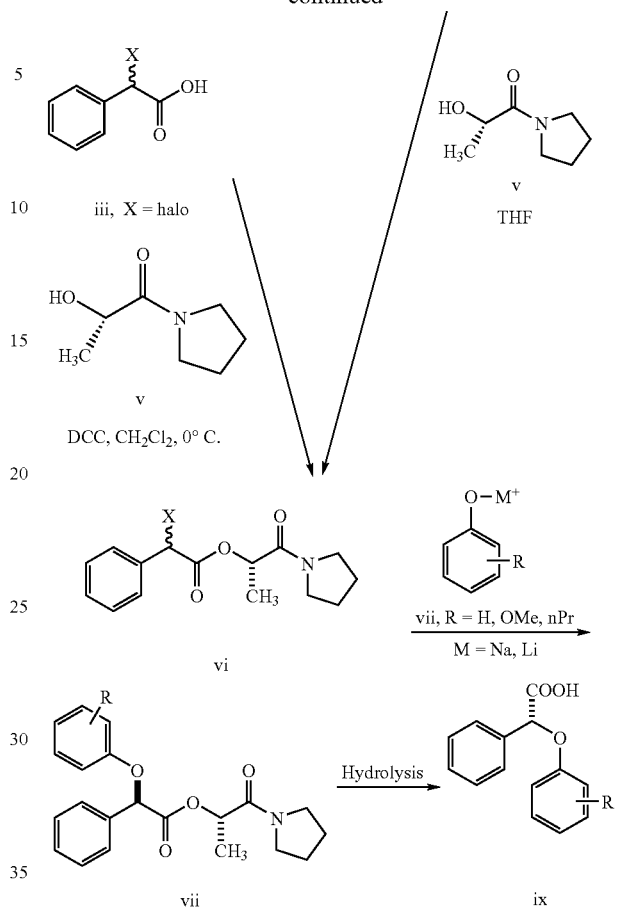

As illustrated in Scheme 1, Devine et al. were able to make α-(phenoxy)phenylacetic acids stereoselectively using a pyrrolidine derived lactamide as a chiral auxiliary (see, U.S. Pat. Nos. 5,708,186 and 5,856,519, the teachings of which are incorporated herein by reference). However this method also has several drawbacks including a) multiple isolation steps and b) low isolated yields. Therefore, there is a need for a more efficient process for producing α-(phenoxy)phenylacetic acid stereoselectively as well as derivatives thereof, e.g., (−)-halofenate. Quite surprisingly, the present invention fulfills this and other needs.

SUMMARY OF THE INVENTION

The present invention provides methods that can be used to reliably convert substituted phenylacetic acids to corresponding (α-(substituted)phenylacetic acid derivatives in high yields and in high enantiomeric purity.

As such, in one embodiment, the present invention provides a method for producing a compound of formula (I):

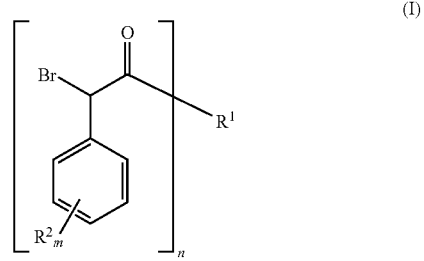

(I)

wherein
R¹ is a member selected from the group consisting of:

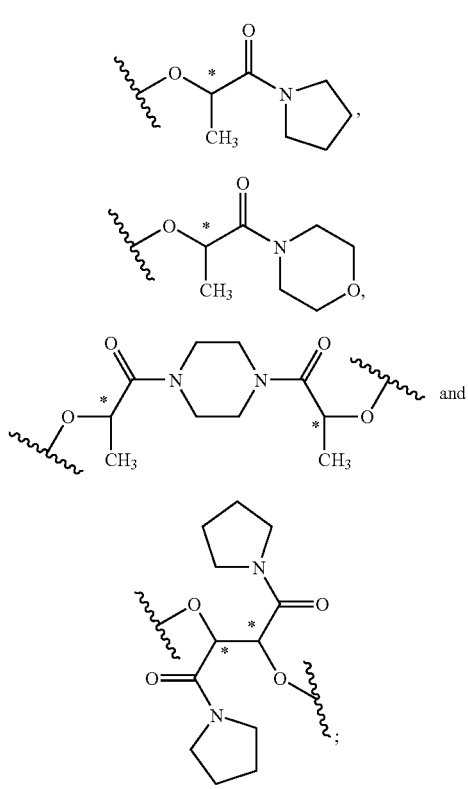

each R² is a member independently selected from the group consisting of $(C_1-C_4)$alkyl, halo, $(C_1-C_4)$haloalkyl, amino, $(C_1-C_4)$aminoalkyl, amido, $(C_1-C_4)$amidoalkyl, $(C_1-C_4)$sulfonylalkyl, $(C_1-C_4)$sulfamylalkyl, $(C_1-C_4)$alkoxy, $(C_1-C_4)$heteroalkyl, carboxy and nitro;
the subscript n is 1 when R¹ has the formula (a) or (b) and 2 when R¹ has the formula (c) or (d);
the subscript m is an integer of from 0 to 3;
* indicates a carbon which is enriched in one stereoisomeric configuration; and
the wavy line indicates the point of attachment of R¹;

the method comprising:

(a) contacting a compound of formula (II):

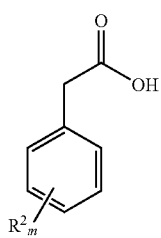

with a carboxylic acid activating reagent selected from the group consisting of a thionyl halide, an anhydride and a thioester generating reagent; in a compatible solvent;

(b) brominating the product of step (a) with bromine in a compatible solvent;

(c) esterifying the product of step (b) with a chiral alcohol selected from the group consisting of:

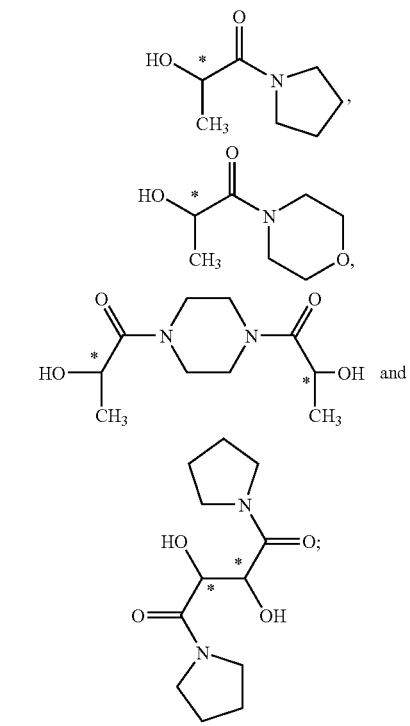

in a compatible solvent.

In another embodiment, the present invention provides α-(substituted)phenylacetic acid compounds of the formula (IV):

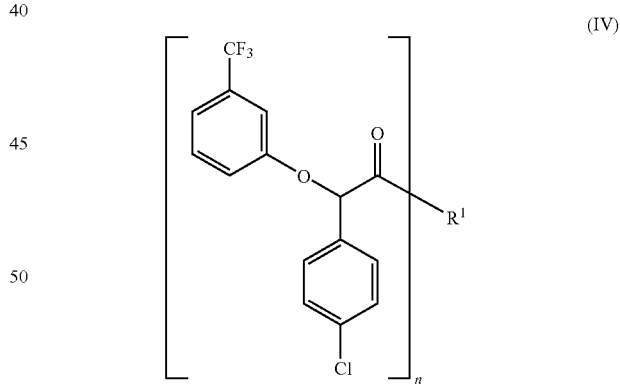

wherein
R¹ is a member selected from the group consisting of:

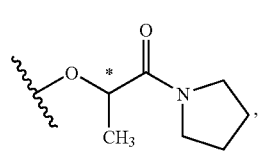

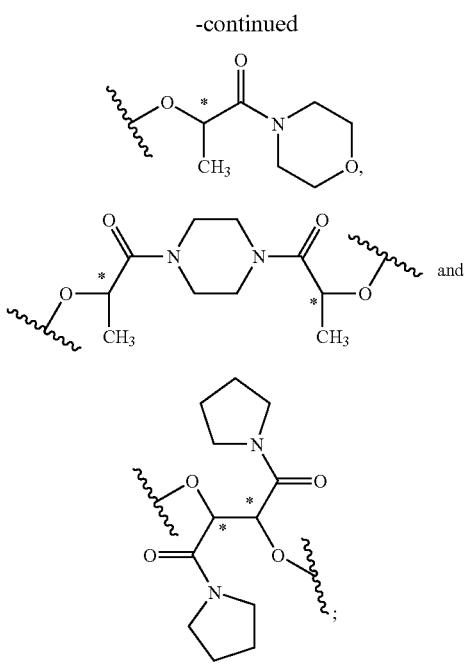

the subscript n is 1 when R¹ has the formula (a) or (b) and 2 when R¹ has the formula (c) or (d);

* indicates a carbon which is enriched in one stereoisomeric configuration; and the wavy line indicates the point of attachment of R¹.

Other features, objects and advantages of the invention and its preferred embodiments will become apparent from the detailed description which follows.

DETAILED DESCRIPTION

I. Definitions

"Alkyl" refers to straight or branched aliphatic hydrocarbons chain groups of one to ten carbon atoms, preferably one to six carbon atoms, and more preferably one to four carbon atoms. Exemplary alkyl groups include, but are not limited to, methyl, ethyl, n-propyl, 2-propyl, tert-butyl, pentyl, and the like.

"Aryl" refers to a monovalent monocyclic or bicyclic aromatic hydrocarbon moiety of 6 to 10 carbon ring atoms. Unless stated or indicated otherwise, an aryl group can be substituted with one or more substituents, preferably one, two, or three substituents, and more preferably one or two substituents selected from alkyl, haloalkyl, nitro, and halo. More specifically the term aryl includes, but is not limited to, phenyl, 1-naphthyl, and 2-naphthyl, and the like, each of which is optionally substituted with one or more substituent(s) discussed above.

"Chiral" or "chiral center" refers to a carbon atom having four different substituents. However, the ultimate criterion of chirality is non-superimposability of mirror images.

The terms "CPTA" and "halofenic acid" are used interchangeably herein and refer to (4-chlorophenyl)(3-trifluoromethylphenoxy)acetic acid.

"Enantiomeric mixture" means a chiral compound having a mixture of enantiomers, including a racemic mixture. Preferably, enantiomeric mixture refers to a chiral compound having a substantially equal amounts of each enantiomers.

More preferably, enantiomeric mixture refers to a racemic mixture where each enantiomer is present in an equal amount.

"Enantiomerically enriched" refers to a composition where one enantiomer is present in a higher amount than prior to being subjected to a separation process.

"Enantiomeric excess" or "% ee" refers to the amount of difference between the first enantiomer and the second enantiomer. Enantiomeric excess is defined by the equation: % ee=(% of the first enantiomer)–(% of the second enantiomer). Thus, if a composition comprises 98% of the first enantiomer and 2% of the second enantiomer, the enantiomeric excess of the first enantiomer is 98%–2% or 96%.

The terms "halide" and "halo" are used interchangeably herein and refer to halogen, which includes F, Cl, Br, and I, as well as pseudohalides, such as —CN and —SCN.

"Haloalkyl" refers to alkyl group as defined herein in which one or more hydrogen atoms have been replaced with halogens, including perhaloalkyls, such as trifluoromethyl.

"Halofenate" refers to 2-acetamidoethyl 4-chlorophenyl-(3-trifluoromethyl-phenoxy)acetate (i.e., 4-chloro-α-(3-(trifluoromethyl)phenoxy)benzeneacetic acid, 2-(acetylamino) ethyl ester or (4-chlorophenyl)(3-trifluoromethylphenoxy) acetic acid), 2-(acetylamino)ethyl ester).

"Heteroalkyl" means a branched or unbranched acyclic saturated alkyl moiety containing one or more heteroatoms or one or more heteroatom-containing substituents, where the heteroatom is O, N, or S. Exemplary heteroatom-containing substituents include =O, —OR$^a$, —C(=O)R$^a$, —NR$^a$R$^b$, —N(R$^a$)C(=O)R$^b$, —C(=O)NR$^a$R$^b$ and —S(O)$_n$R$^a$ (where n is an integer from 0 to 2). Each of R$^a$ and R$^b$ is independently hydrogen, alkyl, haloalkyl, aryl, or aralkyl. Representative examples of heteroalkyl include, for example, N-acetyl 2-aminoethyl (i.e., —CH$_2$CH$_2$NHC(=O)CH$_3$).

The term "metal" includes Group I, II, and transition metals as well as main group metals, such as B and Si.

"Optical purity" refers to the amount of a particular enantiomer present in the composition. For example, if a composition comprises 98% of the first enantiomer and 2% of the second enantiomer, the optical purity of the first enantiomer is 98%.

Unless otherwise stated, the term "phenyl" refers to an optionally substituted phenyl group. Suitable phenyl substituents are same as those described in the definition of "aryl." Similarly, the term "phenoxy" refers to a moiety of the formula —OAr$^a$, wherein Ar$^a$ is phenyl as defined herein. Thus, the term "α-(phenoxy)phenylacetic acid" refers to acetic acid that is substituted on the 2-position with an optionally substituted phenyl and optionally substituted phenoxy moieties.

"Protecting group" refers to a moiety that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

The term "rate" when referring to a formation of a reaction product refers to kinetic and/or thermodynamic rates.

As used herein, the term "treating", "contacting" or "reacting" refers to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as preferred, more preferred and most preferred definitions, if any.

Many organic compounds exist in optically active forms, i.e., they have the ability to rotate the plane of plane-polarized light. In describing an optically active compound, the prefixes R and S are used to denote the absolute configuration of the molecule about its chiral center(s). The prefixes "d" and "l" or (+) and (−) are employed to designate the sign of rotation of plane-polarized light by the compound, with (−) or (l) meaning that the compound is "levorotatory" and with (+) or (d) is meaning that the compound is "dextrorotatory". There is no correlation between nomenclature for the absolute stereochemistry and for the rotation of an enantiomer. For a given chemical structure, these compounds, called "stereoisomers," are identical except that they are mirror images of one another. A specific stereoisomer can also be referred to as an "enantiomer," and a mixture of such isomers is often called an "enantiomeric" or "racemic" mixture. See, e.g., Streitwiesser, A. & Heathcock, C. H., INTRODUCTION TO ORGANIC CHEMISTRY, $2^{nd}$ Edition, Chapter 7 (MacMillan Publishing Co., U.S.A. 1981).

The terms "substantially free of its (+)-stereoisomer," "substantially free of its (+)-enantiomer," are used interchangeably herein and mean that the compositions contain a substantially greater proportion of the (−)-isomer in relation to the (+)-isomer. In a preferred embodiment, the term "substantially free of its (+) stereoisomer" means that the composition is at least 90% by weight of the (−)-isomer and 10% by weight or less of the (+)-isomer. In a more preferred embodiment, the term "substantially free of its (+)-stereoisomer" means that the composition contains at least 99% by weight of the (−)-isomer and 1% by weight or less of the (+)-isomer. In the most preferred embodiment, the term "substantially free of its (+)-stereoisomer" means that the composition contains greater than 99% by weight of the (−)-isomer. These percentages are based upon the total amount of isomers in the composition.

II. Introduction

Although enantiomers of a chiral compound have exact same chemical bonds, the spatial orientation of atoms in enantiomers is different. Thus, one enantiomer of a chiral drug often exerts desired activity with a significantly less side-effect(s) than the other enantiomer. While resolution of racemates is often used in industrial processes for preparation of optically active, i.e., chiral, compounds; chiral synthesis has made an extensive progress in recent years.

The present invention provides a method for synthesizing a α-(halo)phenylacetic acid chiral ester derivative. The chiral ester on the α-(halo)phenylacetic acid directs the alkylation of 3-trifluoromethylphenol to stereoselectively produce α-(phenoxy)phenylacetic acid derivatives. Thus, compounds produced using methods of the present invention are useful in producing α-(phenoxy)phenylacetic acid derivatives such as those disclosed in U.S. patent application Ser. No. 10/656,567 and U.S. Pat. No. 6,262,118 in high yields. In particular, compounds and methods of the present invention are useful in producing (−)-halofenate.

III. Stereoselective Synthesis

As noted above, previous stereoselective processes to produce (−)-halofenate require multiple steps and result in a composition in low yield or is of insufficient optical purity to be commercially viable. However, present inventors have found that under certain conditions disclosed herein, α-(phenoxy)phenylacetic acid compound of a sufficient optical purity can be produced in high yield and high optical purity with few isolation steps. These high yields are unusual since bromination of similar compounds with bromine do not result in high yields (see Harpp et al. *J. Org. Chem.* 40(23): 3420 (1975). Thus, in one aspect, methods of the present invention are based on the surprising and unexpected discovery by the present inventors that substituted phenylacetic acids can be activated, brominated with bromine and esterified to result in a chiral α-halophenyl acetic ester intermediate in high yield.

This intermediate can then be used to stereoselectively produce α-(phenoxy)phenylacetic acid derivatives. In particular, methods of the present invention provide a desired enantiomer of a α-(phenoxy)phenylacetic acid derivative in yields of at least about 40%, preferably at least about 50%, more preferably at least about 60%, and most preferably at least about 70%. In particular, methods of the present invention provide a desired enantiomer of the α-(phenoxy)phenylacetic acid compound in optical purity of at least about 90%, preferably at least about 95%, more preferably at least about 97%, and most preferably at least about 98%.

One method of stereoselectively producing a α-(phenoxy) phenylacetic acid derivatives, such as xiv, is shown generally in Scheme 2 below.

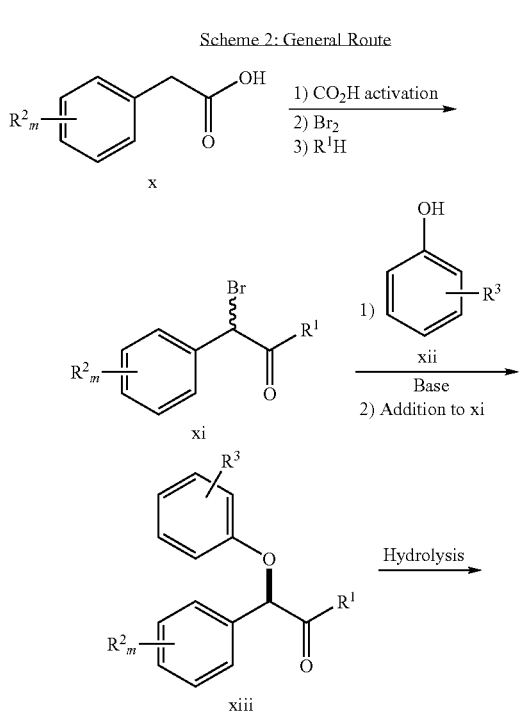

Thus, phenylacetic acid x can be converted to an activated carboxylic acid derivative and subsequently halogenated with molecular bromine to give α-bromophenylacetyl halide xi in two steps. The phenyl acetic acid is preferably a halophenylacetic acid, more preferably 4-halo-phenylacetic acid and more preferably 4-chloro-phenylacetic acid.

Examples of carboxylic activating agents suitable for use in the present invention, include, but are not limited to thionyl halides such as thionyl chloride ($SOCl_2$); anhydrides, such as trifluoroacetic anhydride (TFAA), and thioester generating reagents. The carboxylic acid activating agent is preferably a thionyl halide and more preferably thionyl chloride. It is commercially available as a clear liquid and may be used neat or in a compatible solvent.

The acid halide is then converted to chiral ester xiii, where $R^1$ is a chiral alcohol auxiliary. A wide variety of chiral auxiliaries can be used, including those disclosed in the Examples section below. Preferably, the chiral auxiliary used results in making only one diasteromer of α-(phenoxy)phenylacetic acid. It should be recognized that the chiral alcohol auxiliary compound itself should be of a sufficient enantiomeric purity in order to yield a highly enantiomerically enriched α-(phenoxy)phenylacetic acid derivative. In this manner, one enantiomer at the α-position is readily made, for example, by removing the chiral auxiliary. In one particular embodiment, the chiral auxiliary is an chiral alcohol compound of the formula:

Preferably the chiral alcohol has the formula:

The displacement reaction of ester xi with an appropriately substituted phenol compound xii in the presence of a base, such as a hydroxide gives α-(phenoxy)phenylacetic acid ester xiii. Examples of bases that may be used in the displacement reaction include, but are not limited to hydroxide, such as lithium hydroxide, potassium hydroxide, sodium hydroxide and the like; alkoxide, such as lithium alkoxide, potassium alkoxide, sodium hydroxide and the like; and the like; hydride, such as lithium hydride, potassium hydride, sodium hydride and the like; and the like.

Hydrolysis of the α-(phenoxy)phenylacetic acid ester xiii affords α-(phenoxy)phenylacetic acid xiv. Examples of hydrolyzing agents that may be used include, but are not limited to hydroxide, such as lithium hydroxide, potassium hydroxide, sodium hydroxide and the like; hydroperoxide, such as lithium hydroperoxide, potassium hydroperoxide, sodium hydroperoxoide and the like; and the like.

This synthetic route is shown more specifically in Scheme 3 below:

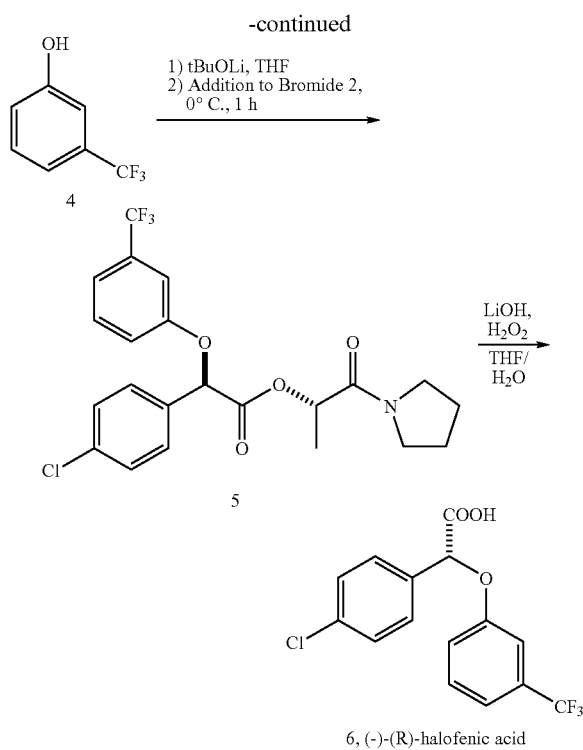

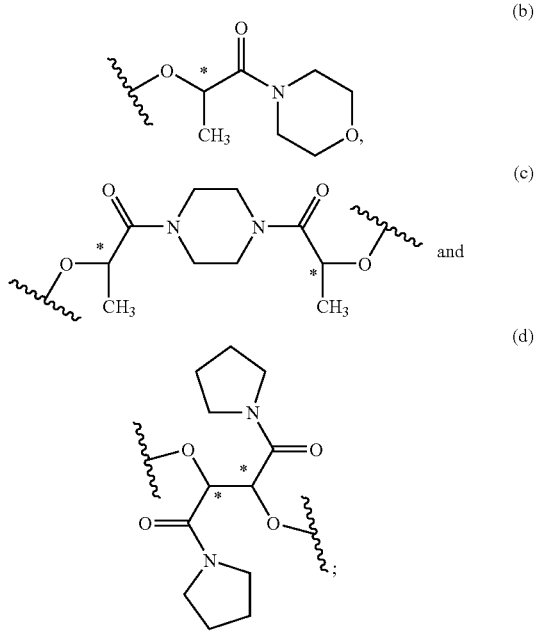

For example, 4-chlorophenylacetic acid 1, can be treated with thionyl chloride to activate the carboxylic acid. This can then be treated with bromine to form 4-chlorophenylacetyl chloride. The esterification is conveniently carried out with (S)—N,N-tetramethylenelactamide 2. This reaction sequence is particularly advantageous as the reactions are conveniently carried out in one reaction vessel with only one isolation step. The displacement reaction of ester 3 with 3-trifluoromethylphenol 4 in the presence of potassium hydroxide gives α-(phenoxy)phenylacetic acid ester 5. Hydrolysis of the α-(phenoxy)phenylacetic acid ester 5 with lithium hydroxide afforded α-(phenoxy)phenylacetic acid 6. In this manner, (4-chlorophenyl)-(3-trifluoromethylphenoxy)-acetic acid, i.e., CPTA, can be prepared in five steps in about 73% yield following crystallization from heptane.

Thus in one embodiment, the present invention provides a method of producing a compound of formula (I):

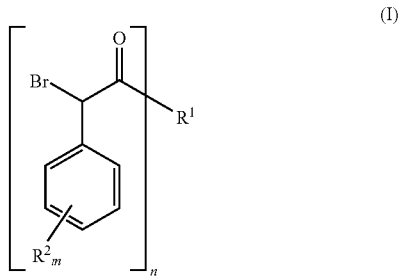

wherein
R$^1$ is a member selected from the group consisting of:

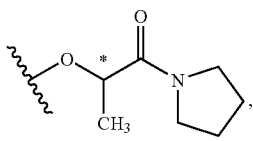

each R$^2$ is a member independently selected from the group consisting of (C$_1$-C$_4$)alkyl, halo, (C$_1$-C$_4$)haloalkyl, amino, (C$_1$-C$_4$)aminoalkyl, amido, (C$_1$-C$_4$)amidoalkyl, (C$_1$-C$_4$)sulfonylalkyl, (C$_1$-C$_4$)sulfamylalkyl, (C$_1$-C$_4$) alkoxy, (C$_1$-C$_4$)heteroalkyl, carboxy and nitro;

the subscript n is 1 when R$^1$ has the formula (a) or (b) and 2 when R$^1$ has the formula (c) or (d);

the subscript m is an integer of from 0 to 3;

* indicates a carbon which is enriched in one stereoisomeric configuration; and the wavy line indicates the point of attachment of R$^1$.

The method generally involves:

(a) activation the carboxylic acid of a compound of formula (II):

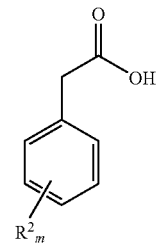

with a carboxylic activating agent in a compatible solvent;

(a) contacting a compound of formula (II):

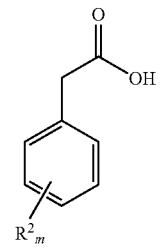

with a carboxylic acid activating reagent selected from the group consisting of a thionyl halide, an anhydride and a thioester generating reagent; in a compatible solvent;

(b) brominating the product of step (a) with bromine in a compatible solvent;

(c) esterifying the product of step (b) with a chiral alcohol selected from the group consisting of:

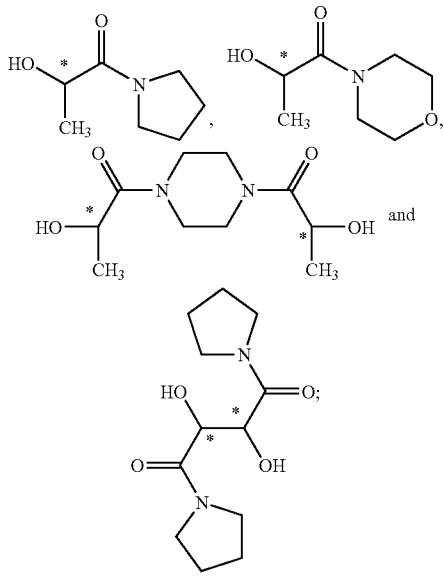

in a compatible solvent.

The present inventors have found that the brominating agent used in the preparation of the α-(phenoxy)phenylacetic acid has a significant effect on ease of isolation and overall yield of the process. For example, when bromine is used in the process of making the α-(phenoxy)phenylacetic acid compound, higher overall yields are obtained than by using other halogenating agents. The amount of halogenating agent used is not particularly important. The amount used is typically more than 1.00 molar equivalent, preferably about 1.5 molar equivalent or more, more preferably about 1.55 molar equivalent.

The reactions are typically conducted in an compatible solvent. A compatible solvent is one which is inert to the reaction conditions and can readily dissolve the reactants. Suitable solvents for the above reactions are known by those of skill in the art. For example, suitable solvents for the carboxylic acid activation, bromination, and esterification reactions include, but are not limited to, aprotic solvents, such as halogenated alkanes, tetrahydrofuran, aromatic hydrocarbons, dialkylethers, and mixtures thereof. A particularly preferred solvent is a halogenated alkane, more preferably 1,2-dichloroethane.

In one embodiment, the bromination process involves heating the reaction mixture to a temperature in the range of from about 70° C. to the boiling point of the solution, preferably from about 80° C. to about 85° C. Heating is carried out until the reaction is complete, which typically ranges from about 1 to about 24 hours, preferably from about 2 to about 18 hours. At lower temperatures, longer reaction times may be needed. It will be readily apparent to those of skill in the art that the progress of this and other reactions in the method of the present invention can be monitored by, for example, HPLC, and the reaction deemed complete when the amount of unreacted starting reagents is less than about 1%.

The bromine can be removed prior to addition of the chiral alcohol auxiliary. This can be done by connecting the reaction vessel to a vacuum pump and removing the bromine under reduced pressure. The pressure, rate and degree of removal is not particularly important.

The solution can be cooled prior to and/or after the chiral alcohol auxiliary is added. This allows for the exothermic nature of the esterification reaction. The rate and amount of cooling of the reaction solution is not particularly important. In one embodiment, the esterification reaction involves cooling the reaction mixture to a temperature in the range of from about 0° C. to room temperature. The reaction is carried out until complete, which typically ranges from about 5 to about 60 minutes, typically about 30 minutes.

In one embodiment, this method can be done in one reaction vessel. In another embodiment, only the final product, the compound of formula (I), is isolated.

In particular, methods of the present invention are directed to intermediates in the synthesis of α-(phenoxy)phenylacetic acids of formula (V):

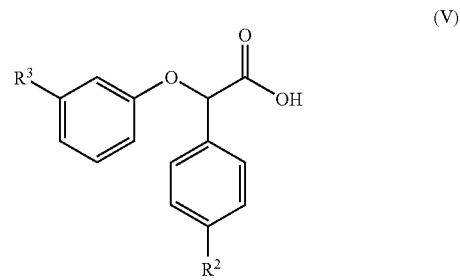

(V)

wherein $R^3$ is haloalkyl and $R^2$ is halide. In one particular embodiment, methods of the present invention are directed to the synthesis of α-(phenoxy)phenylacetic acid of Formula I or, preferably of Formula V, where $R^2$ is chloro. In another embodiment, methods of the present invention are directed to the resolution of α-(phenoxy)phenylacetic acid of Formula I or, preferably, Formula V, where $R^3$ is preferably trifluoromethyl. In yet another embodiment of the present invention, the methods are directed to the stereoselective synthesis of compounds of Formula V wherein $R^2$ is Cl and $R^3$ is $CF_3$ e.g. halofenic acid.

In one particular embodiment, α-(substituted)phenylacetic acid compounds of the formula (IV):

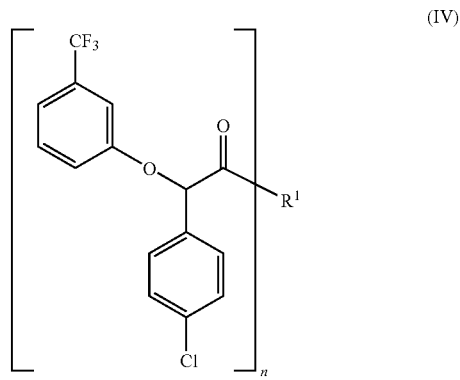

(IV)

wherein
R¹ is a member selected from the group consisting of:

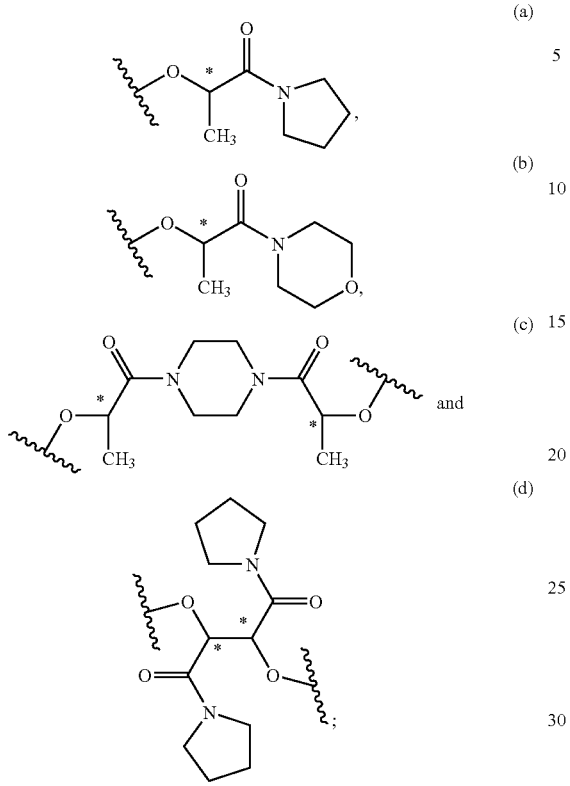

the subscript n is 1 when R¹ has the formula (a) or (b) and 2 when R¹ has the formula (c) or (d);

* indicates a carbon which is enriched in one stereoisomeric configuration; and the wavy line indicates the point of attachment of R¹ are synthesized using the chiral auxiliary. A particularly preferred compound of Formula I and IV above is wherein R¹ is

Unexpectedly, α-(substituted)phenylacetic acid compounds of the formula (IV):

wherein
R¹ is a member selected from the group consisting of:

the subscript n is 1 when R¹ has the formula (a) or (b) and 2 when R¹ has the formula (c) or (d);

* indicates a carbon which is enriched in one stereoisomeric configuration; and the wavy line indicates the point of attachment of R¹;

are produced in high stereoselectivity and in high yield. In order to be economically desirable, methods of the present invention provide at least about 50% yield of the desired enantiomer, preferably at least about 60%, more preferably at least about 70%, and most preferably at least about 75%.

In one embodiment the compound is selected from the group consisting of:

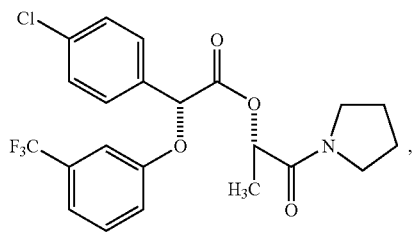
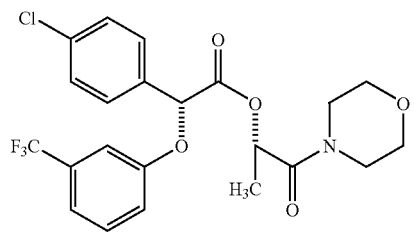
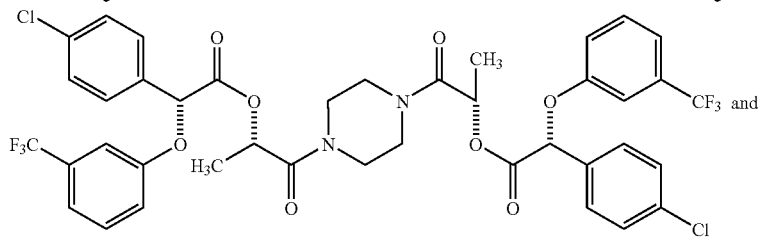
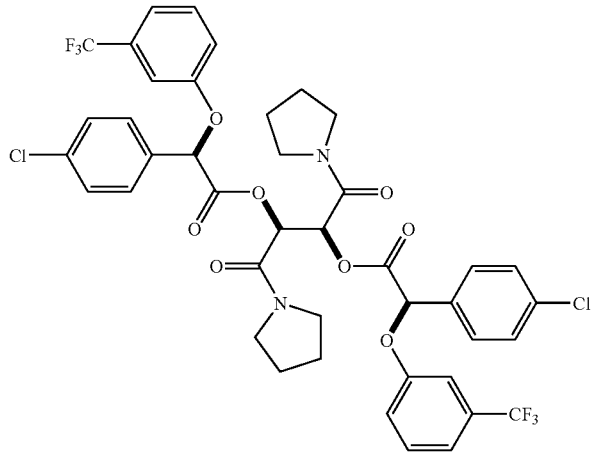
wherein the dashed and bold lines indicate the relative stereochemistry of the compound. In another embodiment the compound is selected from the group consisting of:
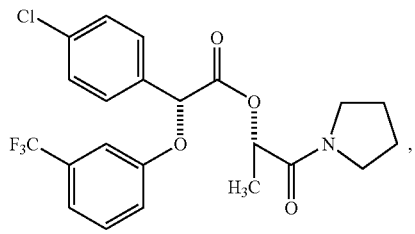
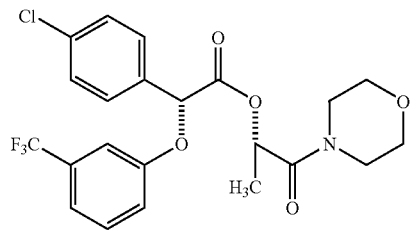
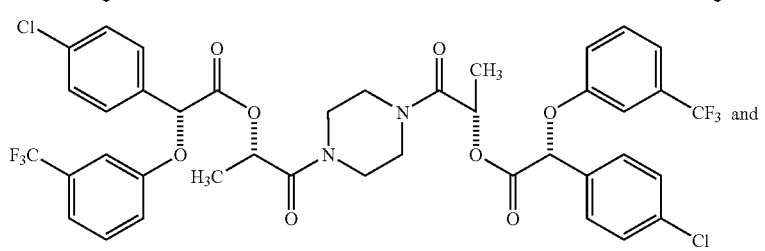

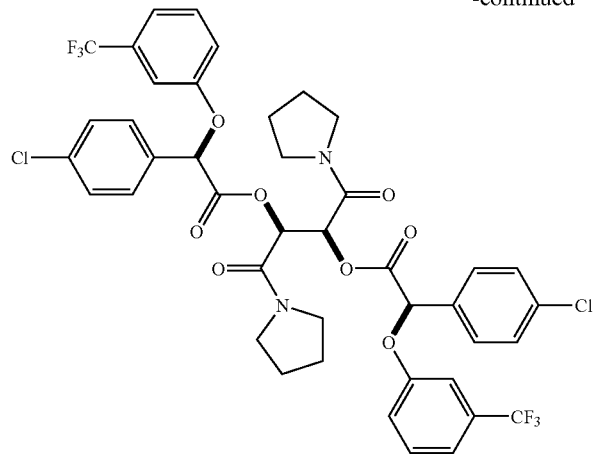

wherein the dashed and bold lines indicate the absolute stereochemistry of the compound.

It should be noted that while methods of the present invention are discussed in reference to the enrichment of the (−)-enantiomer of halofenic acid, methods of the present invention are also applicable for enriching the (+)-enantiomer. The method of the present invention essentially provides a compound enriched in the (−)-enantiomer based on the enantiomeric enrichment of the chiral auxiliary and the stereoselectivity of the reaction. Use of the (+)-enantiomer can be readily accomplished by use of the opposite enantiomer of the chiral alcohol auxiliary. For example, the (+)-enantiomer can be made using (R)—N,N-tetramethylenelactamide.

The chiral auxiliary can be recovered from the above described conversion step and reused/recycled. Thus, the process of the present invention lends itself readily to a recycling-type of procedure.

IV. Synthesis of Chiral Alcohol Auxiliaries

One method of producing a chiral alcohol auxiliary 2 is shown in Scheme 4 below.

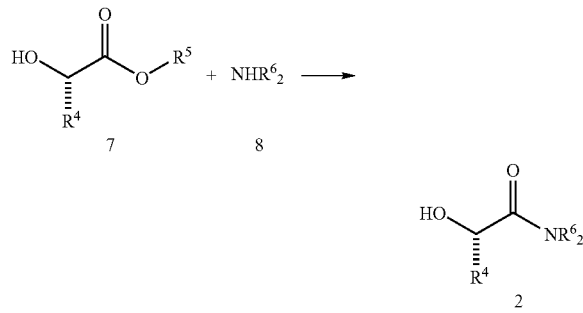

Reaction of lactic ester 7 with an excess of the appropriate cyclic amine gives the chiral auxiliary 2. By using an excess of cyclic amine per equivalent of ester the conversion is high and the amount of racemization is minimized. For example, pyrrolidine 8 (i.e., where $R^6$ is combined to form a five membered ring) is particularly advantageous as pyrrolidine is a good solvent for the lactic ester and the reaction is conveniently carried out neat. In this manner, (S)—N,N-tetramethylenelactamide can be prepared in one step in about 95% yield.

V. Utility of Enantiomerically Enriched α-(Phenoxy)Phenylacetic Acid

Enantiomerically pure α-(phenoxy)phenylacetic acid compounds are useful intermediates in preparing a variety of pharmaceutically active compounds, including α-(phenoxy)phenylacetic acid compounds disclosed in U.S. patent application Ser. No. 10/656,567 and U.S. Pat. No. 6,262,118. Thus, another aspect of the present invention provides a method for enantioselectively producing a α-(phenoxy)phenylacetate compound of the formula:

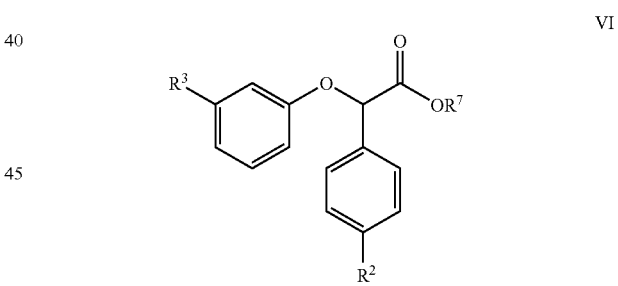

from a α-(phenoxy)phenylacetic acid compound Formula V, wherein $R^3$ is alkyl or haloalkyl, $R^2$ is halo and $R^7$ is heteroalkyl, preferably N-acetyl 2-aminoethyl (i.e., a moiety of the formula —$CH_2CH_2NHC(=O)CH_3$). The method involves stereoselectively synthesizing a α-(phenoxy)phenylacetic acid compound of Formula V as described above and reacting the enantiomerically enriched α-(phenoxy)phenylacetic acid with a carboxylic acid activating reagent. Suitable carboxylic acid activating reagents include thionyl halides (e.g., thionyl chloride), anhydrides (e.g. TFAA), thioester generating reagents, and other carboxylic acid activating reagents known to one skilled in the art.

The activated α-(phenoxy)phenylacetic acid is than reacted with a compound of the formula ($R^7$—O)$_w$M, e.g., N-acetyl ethanolamine derivative, to produce enantiomerically enriched α-(phenoxy)phenylacetate compound of Formula VI, where $R^7$ is as defined above, M is hydrogen or a metal, e.g., Na, K, Li, Ca, Mg, Cs, etc. and the superscript w is the oxidation state of M. The present inventors have discovered that the reaction between the activated acid and the compound of formula $(R^7\text{—O})_w M$ can be carried out without any significant racemization.

Additional objects, advantages, and novel features of this invention will become apparent to those skilled in the art upon examination of the following examples thereof, which are not intended to be limiting.

EXAMPLES

Reagents and Experimental Setup

Unless otherwise stated, reagents and solvents were purchased from Aldrich Chemical or Fisher Scientific. Operations were conducted under a positive nitrogen atmosphere. A Camile process control computer attached to a recirculating heating and cooling system was used to regulate jacket temperatures in the jacketed straight-walled bottom-drain glass reactors. Unless otherwise indicated, solvents were removed using a Buchi rotary evaporator at 15 to 25 torr with a bath temperature of up to 40° C. Solid samples were dried in a vacuum oven at 40° C., 15 to 25 torr. A Cenco HYVAC vacuum pump was used to supply vacuum of less than 1 torr for vacuum distillations. Water levels were determined by Karl Fisher analysis using a Metrohm 756 KF Coulometer and HYDRANAL Coulomat AG reagent. Melting points were determined using a Mettler Toledo FP62 melting point apparatus. pH was measured using a calibrated Orion Model 290A pH meter. Proton and $^{13}$C NMR spectra were recorded on a Bruker Avance 300 MHz spectrometer.

Chiral HPLC analysis was carried out at λ=240 nm by injecting 10 µL of sample dissolved in mobile phase onto a (R,R)WHELK-O 1.5 µm 250×4.6 mm column (Regis Technologies) and eluting with a 1.0 mL/min flow of 95/5/0.4 (v/v/v) hexanes/2-propanol/acetic acid.

Achiral HPLC analysis was carried out at λ=220 nm by injecting 5 µL of sample dissolved in mobile phase onto a Phenomenex LUNA 5 µm C18(2) 250×4.6 mm column at 25° C. A 1.5 mL/min flow of the gradient starting at 66 vol % water/34 vol % acetonitrile/0.1 vol % trifluoroacetic acid and increasing linearly to 26 vol % water/74 vol % acetonitrile/0.1 vol % trifluoroacetic acid at 20 minutes was used.

For analysis of acidic solutions of esters, such as halofenate, acetonitrile was used as the injection solvent. When determined, product concentrations for halofenate were evaluated by HPLC assay using the external standard method and the achiral analysis procedure at sample concentrations of less than 2.5 mg/mL.

Example 1

Synthesis of a Chiral Alcohol Auxiliary (S)—N,N-Tetramethylenelactamide (2)

Pyrrolidine (120 g, 1.69 mol; 2 eq.) was added dropwise to 100 g (0.847 mol) of ethyl (S)-(−)-lactate at 0° C. and stirred at room temperature for 3 days. After removal of excess pyrrolidine and resulting ethanol in vacuo, the oil residue was purified with distillation (104° C., 2 mmHg) to give 113 g (93%) of (S)—N,N-tetramethylenelactamide (2) as a pale-yellow oil. $^1$H NMR (CDCl$_3$): δ 4.30 (1H, q, J=6.63 Hz), 3.74 (1H, br, OH), 3.31-3.61 (4H, m), 1.85-2.03 (4H, m), 1.34 (1H, d, J=6.24 Hz) ppm.

Example 2

Preparation of (−)-Halofenate (6)

Preparation of Compound (3)

To a 2-L 3-neck flask under air, immersed in an oil bath and fitted with an addition funnel and a condenser was added 500 mL of anhydrous 1,2-dichloroethane, 4-chlorophenylacetic acid (174.04 g 98%, 1.0 mol (Acros)) of in one-portion, DMF (0.40 mL, ca. 0.5 mol %) in one-portion and thionyl chloride (95 mL, 1.3 mol, 1.3 eq.) over ~1 minute. The resulting mixture was heated to 70° C. (oil-bath temperature) over 15 minutes. Vigorous gas evolution began approximately 5 minutes after heating (at ~40-45° C.). The vigorous gas evolution slowed to a steady stream and then the gas evolution stopped. After stirring at 70° C. for 2 hours, bromine (80 mL, ca. 249 g, 1.55 mol; 1.55 eq.) was added to the resulting pale yellow solution (at 65° C.) over ~1 minute to give a brown solution. The reaction was stirred at 80° C. to 85° C. (oil-bath temperature) overnight (ca. 18 hours) and then cooled to room temperature. This α-bromo acid chloride solution was stored at room temperature and used in the next ester formation step without further purification.

The solution of crude acid chloride (138 g, ~0.138 mol) in 1,2-dichloroethane prepared above was diluted with 100 mL of 1,2-dichloroethane. Excess bromine was removed by distillation in vacuo until ca. 100 mL of solution remained. The acid chloride solution was then added dropwise to a solution of (S)—N,N-tetramethylenelactamide (20.1 g, 0.140 mol) and triethylamine (14.78 g, 0.147 mol) in 100 mL of 1,2-dichloroethane at 0° C. The resulting brown mixture was warmed up to room temperature over 1 h. The reaction mixture was quenched with water (100 mL), and the organic layer was separated and washed with 100 mL of 10% Na$_2$S$_2$O$_3$ and then with saturated NaHCO$_3$ (100 mL). The organic layer was dried over Na$_2$SO$_4$ and then concentrated in vacuo to give 45.8 g of crude product as a brown oil which was used in the next step without further purification.

Preparation of Compound (6)

To a solution of α,α,α-trifluoro-m-cresol (3.3 g; 0.0204 mol) in anhydrous THF (20 mL) at room temperature was added dropwise lithium tert-butoxide (20 µL of a 1.0 M solution in THF; 0.02 mol). The resulting lithium phenoxide solution was added dropwise to a solution of bromide 3 (crude, 7.5 g; 0.02 mol) in 40 mL of THF at −5° C. After stirring at −5° C. for 1 hour, a pre-mixed solution of hydrogen peroxide (Fisher 30%; 105 mL, 0.4 mol) and LiOH.H$_2$O (21 g, 0.05 mol) in water (50 mL) was added at room temperature over 20 min. The reaction was stirred at 0-4° C. for 1 hour, quenched with saturated aqueous sodium bisulfite (150 mL), then 1N HCl was added to adjust the pH of the solution to about 2. THF was removed by distillation in vacuo, and then the reaction mixture was diluted with EtOAc (100 mL). The organic layer was washed with water and brine, dried over Na$_2$SO$_4$ and evaporated to give 7 g of crude acid. The crude acid was crystallized from heptane to give 4.6 g of a white solid. Chiral HPLC analysis 96.5:3.5 enantiomers.

Preparation of halofenic acid can be carried out using similar conditions with other chiral auxiliaries listed above.

Example 3

Alternative Preparation of Halofenate (6)

To a solution of α,α,α-trifluoro-m-cresol (6.71 g; 0.041 mol) in anhydrous THF (20 mL) and toluene (30 mL) at room temperature was added lithium hydroxide hydrate (1.68 g, 40 mmol). The solvent was removed after 1 hr and the residue was dissolved in 30 mL anhydrous THF (30 mL). The resulting lithium phenoxide solution was added dropwise to a solution of bromide 3 (crude, 14.9 g; 0.04 mol) and NaI (0.3 g) in 100 mL of THF with stirring at room temperature for 1 h at −5° C. and for an additional 3 hr. at −5° C. to 0° C. $^1$H NMR showed the disappearance of bromide 3.

Hydrogen peroxide (Fisher 30%; 209 mL, 0.8 mol) was added to a solution of lithium hydroxide (4.2 g, 0.09 mol) in water (100 mL), and the mixture was stirred at room temperature for 20 min. This solution was then slowly added to a cold solution of lactamide 4 in THF at 0° C. The reaction was stirred at 0-4° C. for 1 hour, quenched with 1N HCl and adjusted pH to 2. THF was removed by distillation in vacuo and then the reaction mixture was diluted with EtOAc (150 mL). The organic layer was washed with water, saturated $Na_2S_2O_3$ and brine, dried over $Na_2SO_4$ and evaporated to give crude acid. The crude acid was crystallized from heptane to give 8.4 g of a white solid. (99:1 enantiomers, determined by chiral HPLC).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for preparing a compound of formula (I):

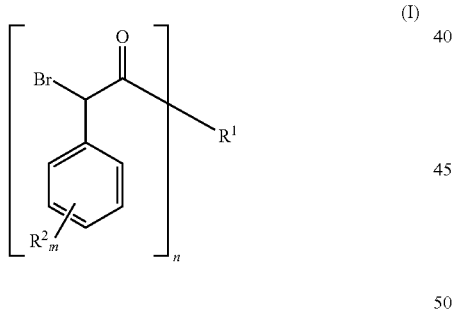

(I)

wherein
R$^1$ is a member selected from the group consisting of:

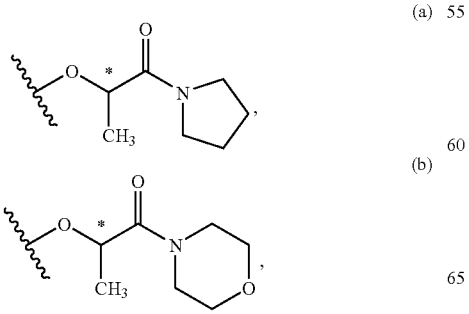

(a)

(b)

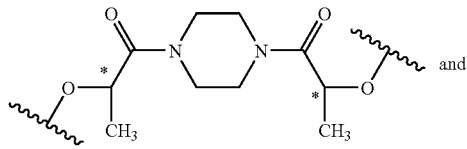

(c)

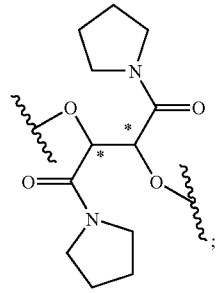

(d)

each R$^2$ is a member independently selected from the group consisting of $(C_1-C_4)$alkyl, halo, $(C_1-C_4)$haloalkyl, amino, $(C_1-C_4)$aminoalkyl, amido, $(C_1-C_4)$amidoalkyl, $(C_1-C_4)$sulfonylalkyl, $(C_1-C_4)$sulfamylalkyl, $(C_1-C_4)$alkoxy, $(C_1-C_4)$heteroalkyl, carboxy and nitro;

the subscript n is 1 when R$^1$ has the formula (a) or (b) and 2 when R$^1$ has the formula (c) or (d);

the subscript m is an integer of from 0 to 3;

* indicates a carbon which is enriched in one stereoisomeric configuration; and the wavy line indicates the point of attachment of R$^1$;

the method comprising:

(a) contacting a compound of formula (II):

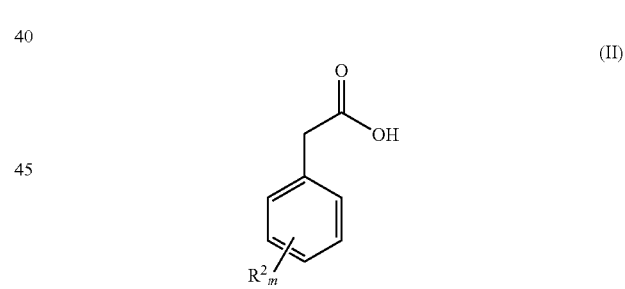

(II)

with a carboxylic acid activating reagent selected from the group consisting of thionyl halides, anhydrides and thioester generating reagents; in a compatible solvent;

(b) brominating the product of step (a) with bromine in a compatible solvent;

(c) esterifying the product of step (b) with a chiral alcohol selected from the group consisting of:

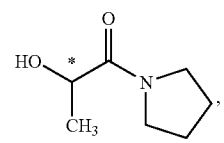

-continued

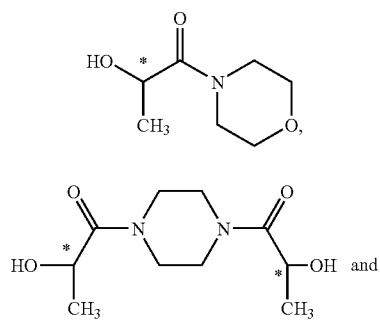

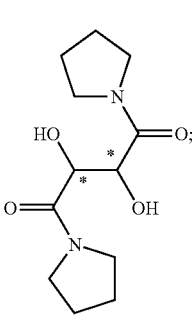

in a compatible solvent to stereoselectively produce a compound of formula (I).

2. The method of claim 1, wherein $R^1$ is

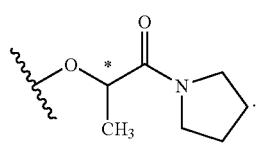

3. The method of claim 1, wherein the compound of formula (II) is 4-chlorophenylacetic acid.

4. The method of claim 1, wherein the carboxylic acid activating reagent is thionyl halide.

5. The method of claim 1, wherein the carboxylic acid activating reagent is thionyl chloride.

6. The method of claim 1, wherein bromine is present in a concentration of about at least 1 molar equivalent to the amount of the compound of formula (II).

7. The method of claim 1, wherein the solvent is a halogenated alkane solvent.

8. The method of claim 1, wherein the solvent is 1,2-dichloroethane.

9. The method of claim 1, wherein said brominating is carried out at a temperature of at least about 70° C.

10. The method of claim 1, further comprising removing excess bromine under reduced pressure before said step (c).

11. The method of claim 1, wherein the method is conducted in one reaction vessel.

12. The method of claim 1, wherein only the compound of Formula (I) is isolated.

13. A method for preparing a compound of formula (I):

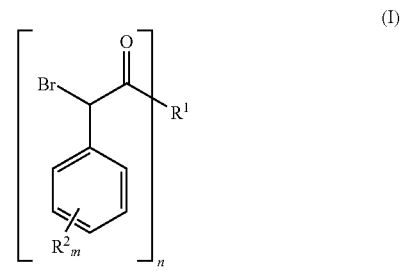

wherein $R^1$ is a member selected from the group consisting of:

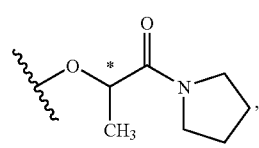

(a)

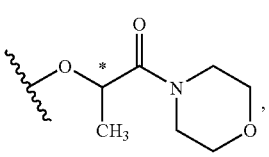

(b)

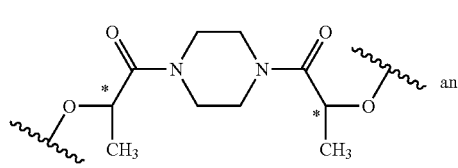

(c)

and

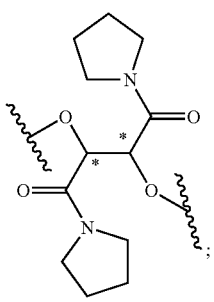

(d)

each $R^2$ is a member independently selected from the group consisting of $(C_1\text{-}C_4)$alkyl, halo, $(C_1\text{-}C_4)$haloalkyl, amino, $(C_1\text{-}C_4)$aminoalkyl, amido, $(C_1\text{-}C_4)$amidoalkyl, $(C_1\text{-}C_4)$sulfonylalkyl, $(C_1\text{-}C_4)$sulfamylalkyl, $(C_1\text{-}C_4)$alkoxy, $(C_1\text{-}C_4)$heteroalkyl, carboxy and nitro;

the subscript n is 1 when $R^1$ has the formula (a) or (b) and 2 when $R^1$ has the formula (c) or (d);

the subscript m is an integer of from 0 to 3;

* indicates a carbon which is enriched in one stereoisomeric configuration; and the wavy line indicates the point of attachment of $R^1$;

the method comprising esterifying a compound of the formula:

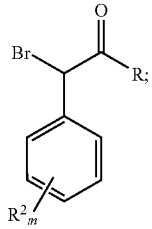

wherein R is a halide, or when combined with the carbonyl to which it is attached is an anhydride or thioester group; in a compatible solvent with a chiral alcohol selected from the group consisting of:

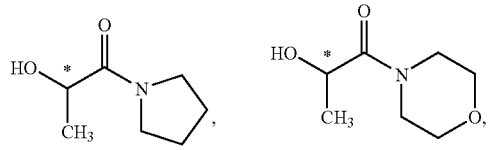

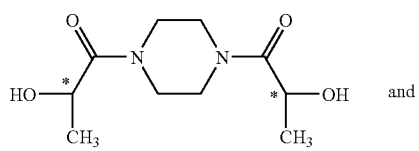

and

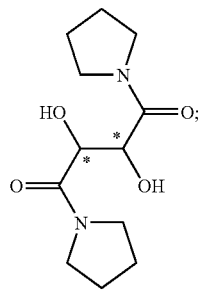

in a compatible solvent to stereoselectively produce a compound of formula (I).

14. A method for preparing (−)-halofenate comprising i) preparing a compound of formula (I):

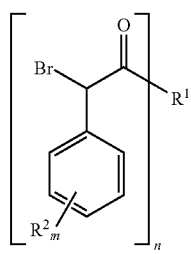
(I)

wherein
$R^1$ is a member selected from the group consisting of:

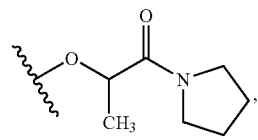
(a)

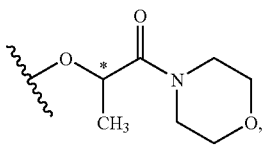
(b)

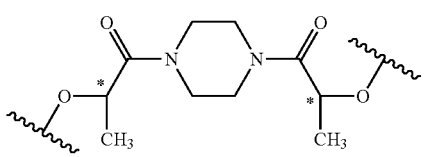
and
(c)

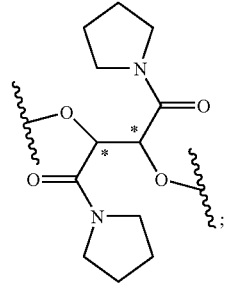
(d)

each $R^2$ is a member independently selected from the group consisting of $(C_1-C_4)$alkyl, halo, $(C_1-C_4)$haloalkyl, amino, $(C_1-C_4)$aminoalkyl, amido, $(C_1-C_4)$amidoalkyl, $(C_1-C_4)$sulfonylalkyl, $(C_1-C_4)$sulfamylalkyl, $(C_1-C_4)$alkoxy, $(C_1-C_4)$heteroalkyl, carboxy and nitro;

the subscript n is 1 when $R^1$ has the formula (a) or (b) and 2 when $R^1$ has the formula (c) or (d);

the subscript m is an integer of from 0 to 3;

* indicates a carbon which is enriched in one stereoisomeric configuration; and the wavy line indicates the point of attachment of $R^1$;

the method comprising:

(a) contacting a compound of formula (II):

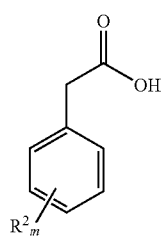
(II)

with a carboxylic acid activating reagent selected from the group consisting of thionyl halides, anhydrides and thioester generating reagents; in a compatible solvent;

(b) brominating the product of step (a) with bromine in a compatible solvent;

(c) esterifying the product of step (b) with a chiral alcohol selected from the group consisting of:

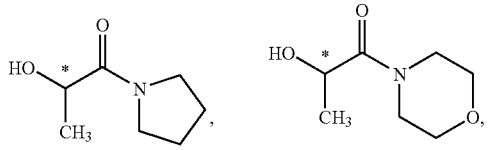

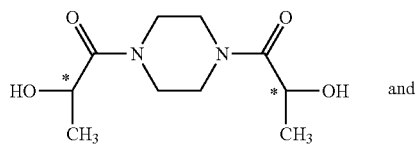

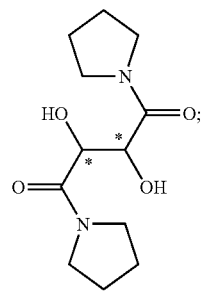

in a compatible solvent to stereoselectively produce a compound of formula (I); and further converting the product of said step(s) to (−)-halofenate.

15. A method for preparing (−)-halofenate comprising i) preparing a compound of formula (I):

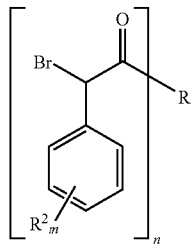

wherein
R¹ is a member selected from the group consisting of:

(a)
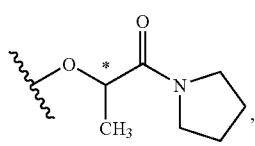

(b)
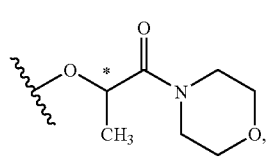

-continued (c)
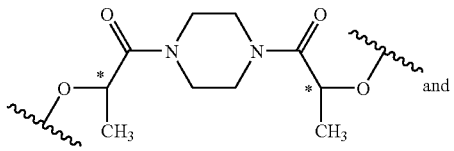
and (d)
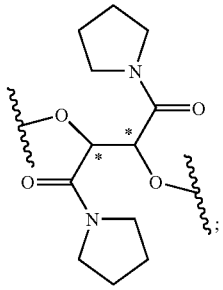

each R² is a member independently selected from the group consisting of $(C_1-C_4)$alkyl, halo, $(C_1-C_4)$haloalkyl, amino, $(C_1-C_4)$aminoalkyl, amido, $(C_1-C_4)$amidoalkyl, $(C_1-C_4)$sulfonylalkyl, $(C_1-C_4)$sulfamylalkyl, $(C_1-C_4)$alkoxy, $(C_1-C_4)$heteroalkyl, carboxy and nitro;
the subscript n is 1 when R¹ has the formula (a) or (b) and 2 when R¹ has the formula (c) or (d);
the subscript m is an integer of from 0 to 3;
* indicates a carbon which is enriched in one stereoisomeric configuration; and
the wavy line indicates the point of attachment of R¹;
the method comprising:
(a) contacting a compound of formula (II):

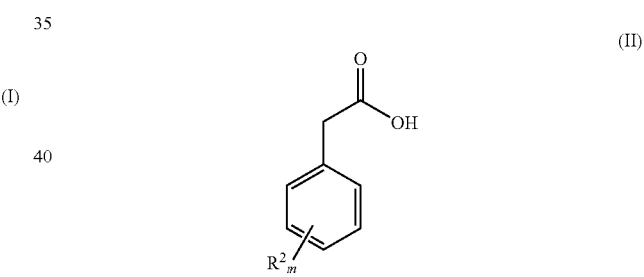

with a carboxylic acid activating reagent selected from the group consisting of thionyl halides, anhydrides and thioester generating reagents; in a compatible solvent;
(b) brominating the product of step (a) with bromine in a compatible solvent; and further converting the product of said step(s) to (−)-halofenate.

16. A method for preparing (−)-halofenate comprising i) preparing a compound of formula (I):

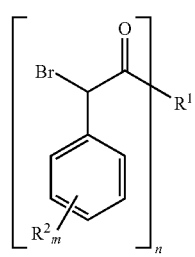

wherein

R¹ is a member selected from the group consisting of:

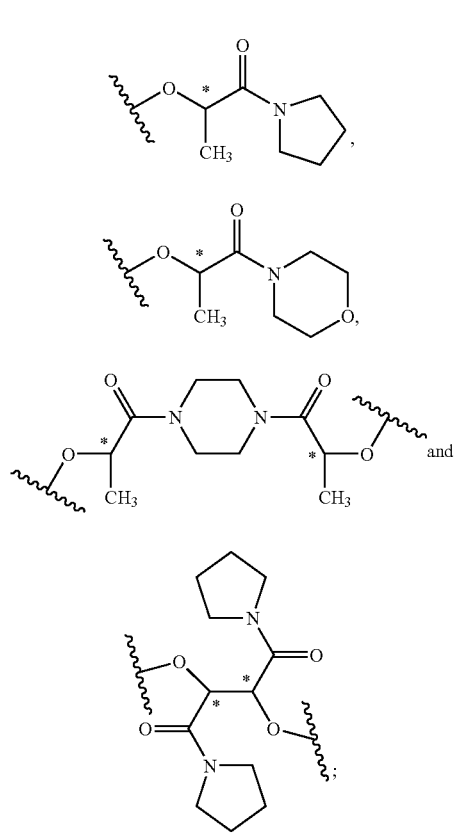

each R² is a member independently selected from the group consisting of (C₁-C₄)alkyl, halo, (C₁-C₄)haloalkyl, amino, (C₁-C₄)aminoalkyl, amido, (C₁-C₄)amidoalkyl, (C₁-C₄)sulfonylalkyl, (C₁-C₄)sulfamylalkyl, (C₁-C₄)alkoxy, (C₁-C₄)heteroalkyl, carboxy and nitro;

the subscript n is 1 when R¹ has the formula (a) or (b) and 2 when R¹ has the formula (c) or (d);

the subscript m is an integer of from 0 to 3;

* indicates a carbon which is enriched in one stereoisomeric configuration; and the wavy line indicates the point of attachment of R¹;

the method comprising esterifying a compound of the formula:

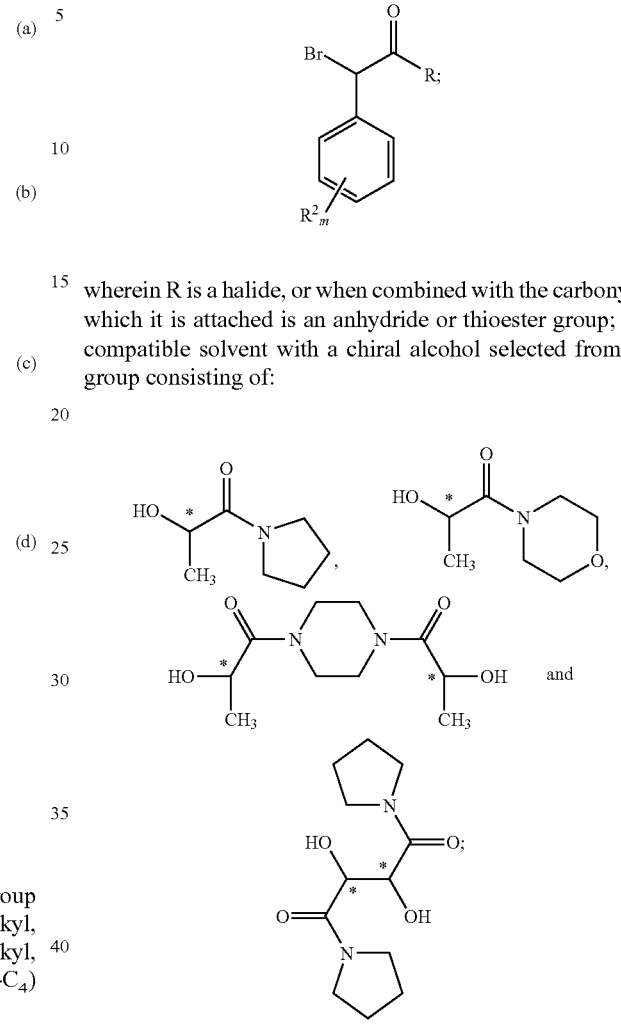

wherein R is a halide, or when combined with the carbonyl to which it is attached is an anhydride or thioester group; in a compatible solvent with a chiral alcohol selected from the group consisting of:

in a compatible solvent to stereoselectively produce a compound of formula (I); and further converting the product of said step(s) to (−)-halofenate.

* * * * *